US006776758B2

(12) United States Patent
Peszynski et al.

(10) Patent No.: US 6,776,758 B2
(45) Date of Patent: Aug. 17, 2004

(54) RFI-PROTECTED ULTRASOUND PROBE

(75) Inventors: Michael Eugene Peszynski, Newburyport, MA (US); David Chang Garner, Somerville, MA (US); Timothy J. Savord, Lowell, MA (US); Roger Dugas, Chester, NH (US); Hubert Yeung, Santa Rosa, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/270,344

(22) Filed: Oct. 11, 2002

(65) Prior Publication Data

US 2004/0073118 A1 Apr. 15, 2004

(51) Int. Cl.[7] ................................................. A61B 8/00
(52) U.S. Cl. ...................................................... 600/437
(58) Field of Search ................................ 600/459, 437, 600/462, 142, 472; 174/110; 128/916

(56) References Cited

U.S. PATENT DOCUMENTS 4,543,960 A * 10/1985 Harui et al. ................. 600/462
5,127,410 A * 7/1992 King et al. .................. 600/459
5,297,553 A * 3/1994 Sliwa et al. ................. 600/459
5,552,565 A * 9/1996 Cartier et al. ............. 174/117 F
5,555,887 A * 9/1996 Fraser et al. ................ 600/472
5,626,138 A * 5/1997 Hossack et al. ............ 600/459
6,364,828 B1 * 4/2002 Yeung et al. ............... 600/142
6,497,667 B1 * 12/2002 Miller et al. ................ 600/459

* cited by examiner

Primary Examiner—Mary Beth Jones
Assistant Examiner—Ruby Jain
(74) Attorney, Agent, or Firm—John F. Vodopia

(57) ABSTRACT

An ultrasound imaging system including an electromagnetically protected ultrasound TEE probe, a display for displaying ultrasound images, a housing including a transducer connector including at least one connection and a computer for processing electrical signals representative of received ultrasound echoes. The TEE probe includes a probe housing including an imaging sensor, an outer acoustic lens, a cable interconnect and an internal metal shield which surrounds the sensor and cable interconnect, and a cable including electrical conductors and electromagnetic cable shielding, the electrical conductors electrically connected to the cable interconnect at a first end, and the electrical conductors and the cable shielding are electrically connected to a transducer connector at a second end.

28 Claims, 6 Drawing Sheets

RFI-PROTECTED ULTRASOUND PROBE

FIELD OF THE INVENTION

The present invention generally relates to ultrasonic transducers, and in particular relates to the protection of ultrasonic probes from electromagnetic (EM) or radio frequency (RF) interference.

BACKGROUND OF THE INVENTION

Ultrasound diagnostic technology generally relates to imaging of biological tissue within an animal body, typically human, using an ultrasound transducer. An ultrasound transducer transmits ultrasonic waves into the tissue and receives ultrasonic echoes which are reflected from the tissue. The transducer may be placed on a body surface or inserted into a patient's body in a selected imaging region, for example, the esophagus. Simply described, transducers include ultrasound sensors, a housing and cabling to connect the transducer to the rest of the ultrasound imaging system. Sensors may be described as including one or more piezoelectric elements, impedance matching material (stack) and required mechanical components. There are single element sensors (single channel), and multi-element sensors (multi-channel), comprising sensor arrays, which actually generate and direct ultrasonic waves to the imaging region. More particularly, piezoelectric element(s) in the transducer sensor portion transmit the ultrasonic waves and then receive the return echoes reflected from the imaging region. The piezoelectric elements contained in the transducer convert the received acoustic waves into electrical signals that are processed to form a diagnostic image.

Transesophageal echocardiography (TEE) probes are specific ultrasound transducers which are used endoscopically, for example, for ultrasonic imaging of the heart. Ultrasound imaging of the heart is always a difficult task because the heart is located in the thoracic cavity surrounded by the ribs and lungs. Ultrasound imaging through the ribs is difficult because of the absorptive and reflective characteristics of the bone structure comprising the ribs. This requires access through any of several intercostal windows, but even the transmission and reception of ultrasound through intercostal windows may provide ultrasound data with limited clinical use.

TEE probes were developed through application of the general body of endoscopic technology (introduction of medical devices into the body) to ultrasound in order to overcome the problems associated with imaging thoracic organs mentioned briefly above. TEE probes include an ultrasonic sensor located at the end or tip of an elongated probe housing. The TEE probe may be passed through the patient's mouth into the esophagus or stomach. When inserted orally into the stomach or esophagus within the thoracic cavity, the ribs no longer pose an impediment to the transmission and reception of ultrasound signals. The typical TEE probe includes a control mechanism external to the body, enabling the clinician to manipulate the end of the probe so that the sensor or transducer array at the end or tip of the probe is directed as desired towards, for example, the heart, and is a significant improvement in the use of ultrasound to diagnose the heart.

U.S. Pat. No. 4,543,960, the contents of which are incorporated herein by reference, teaches a TEE ultrasound transducer probe in which a phased array or linear array of transducer elements is mounted on a rotating base inside the probe assembly. As shown in the drawings accompanying the patent, the transducer array is formed of a rectangular shaped array of piezoelectric elements mounted on a cylindrical rotateable base. A pulley is mounted on a shaft extending from the rotateable base, whereby the transducer array and base may be rotated inside the probe assembly varying the imaging plane. Improvements to U.S. Pat. No. 4,543,960 are described in U.S. Pat. No. 5,226,422, include a circular array transducer using improved grounding techniques, a bell-shaped housing for the transducer and a bubble trap for the transducer components, also incorporated herein in its entirety.

U.S. Pat. No. 5,555,887, commonly owned and incorporated herein in its entirety, discloses a TEE probe (or transducer probe assembly) which includes a removable articulating tip which allows the clinician to change the acoustic performance simply by replacing the probe tip. The articulation mechanism includes a plurality of links which snap together to form a continuous, torsionally stiff articulating joint. The joint has built in angulation stops and exhibits substantially no torsional play when loaded. The transducer in the probe assembly, more particularly, the probe tip, is rotated by a motor driven mechanism with two speeds of rotation. The transducer includes heat dissipating means for taking heat away from the Transducer probe.

TEE probes have been found to be useful in imaging the heart chambers in the operating room (OR) during surgical procedures, particularly in surgical interventions. OR imaging, however, must address the problem of electrical noise generated by surgical instrument use. For example, surgical procedure are often accompanied with surgical interventions including the use of electro-surgical units (ESUs) (e.g., cauterizing instruments). ESUs often generate high levels of broad spectrum electromagnetic energy which is dispersed into the surrounding environment, and are typically radiating at less than a body's length away from a TEE or other transducer probe. This broad spectrum radiation dispersed by an active ESU, as well as other electromagnetic or RF noise (e.g., telemetry signals), may be coupled into the ultrasound equipment in the OR, or other clinical setting.

Conventional ultrasound systems are known to inadvertently receive such noise via whatever antenna-like apparatus (e.g., cables, interconnects) or antenna-emulating circuitry included in the ultrasound equipment. TEE probes are inherently good receiving antenna, because they include a relatively long cable connected between the probe and imaging system. The end result in any case is an inability of ultrasound diagnostic imaging to be utilized during ESU usage, or other high noise environments. This may include pre-operative assessment, postoperative assessment, or any time during actual surgery or other interventional procedure where an ESU or other noise generators are operating.

While attempts have been made to shield transducers from broadband RF radiation, no efforts are known heretofore to be effective, particularly for transducers or transducer probes used in the OR concurrently with the used of interventional equipment. Insufficient or incomplete electric shielding allows RF or EM energy to be coupled onto ultrasound coaxial and other electrical cables and circuits found within transducer housings. The coupled (received) energy makes its way into the ultrasound imaging system. If signal filters are not employed (which are not only expensive but take up precious space), ESU or other noise will be processed along with non-rejected imaging data and displayed on the imaging system display, complicating diagnoses.

OBJECTS AND SUMMARY OF THE INVENTION

It is therefore an object of this invention to provide an electromagnetically shielded transducer and/or transducer probe, as well as their respective assemblies, in order to avoid electromagnetic interference (EMI), for example, interference from radio frequency (RF) signals, RF interference or interference from electrical signals.

It is therefore an object of this invention to provide an electromagnetically shielded transducer and/or transducer probe, as well as their respective assemblies, in order to avoid any EM interference, regardless of its source or species, and particularly that generated proximate an ultrasound probe/system such as OR equipment (e.g., an ESU).

It is another object of this invention to provide an electromagnetically shielded transducer probe and/or assembly which is effectively shielded from EMI (RFI). We define transducer probe herein as a species of transducer, where TEE probes are a species of transducer probe.

It is another object of the invention to provide a transducer probe which is sufficiently shielded to essentially eradicate noise broad band, for example, at least 100 dB down broad spectrum, or at least at frequencies where particularly troubling noise may be found, e.g., frequency emitted from an ESU, as well as flexible enough in its gastroscopic portions to be useful.

One embodiment of this invention includes a transducer or transducer assembly in which all transducer components, which may include the sensor, sensor stack, transducer array, sensor interconnects, cabling housing and system interconnects, are entirely shielded. Any shield comprising what may be referred to as a system of shield to entirely shield every transducer component is preferably connected to ground (whether floating or earth ground) to minimize the impedance of the shield to current flow, thereby maximizing the shielding effect of same.

One embodiment of a transducer probe of this invention include that every component from a transducer connector to the endoscopic portion be completely shielded whereby the shield is implemented in such a manner as to maintain maximum flexibility.

BRIEF DESCRIPTION OF THE DRAWING FIGURES

FIG. 1 is a schematic depiction of a first embodiment of an ultrasound system of this invention, including a transducer with integral EMI shielding, where the entire ultrasound system is protected from electromagnetic interference;

FIG. 2 a transducer included in the ultrasound system embodiment of FIG. 1, where all of the internally housed transducer components are entirely electromagnetically shielded, and the shielding is connected to earth ground; and FIGS. 3A, 3B show rectangular shielding patterns comprising circular and rectangular apertures, respectively;

Figure 4:
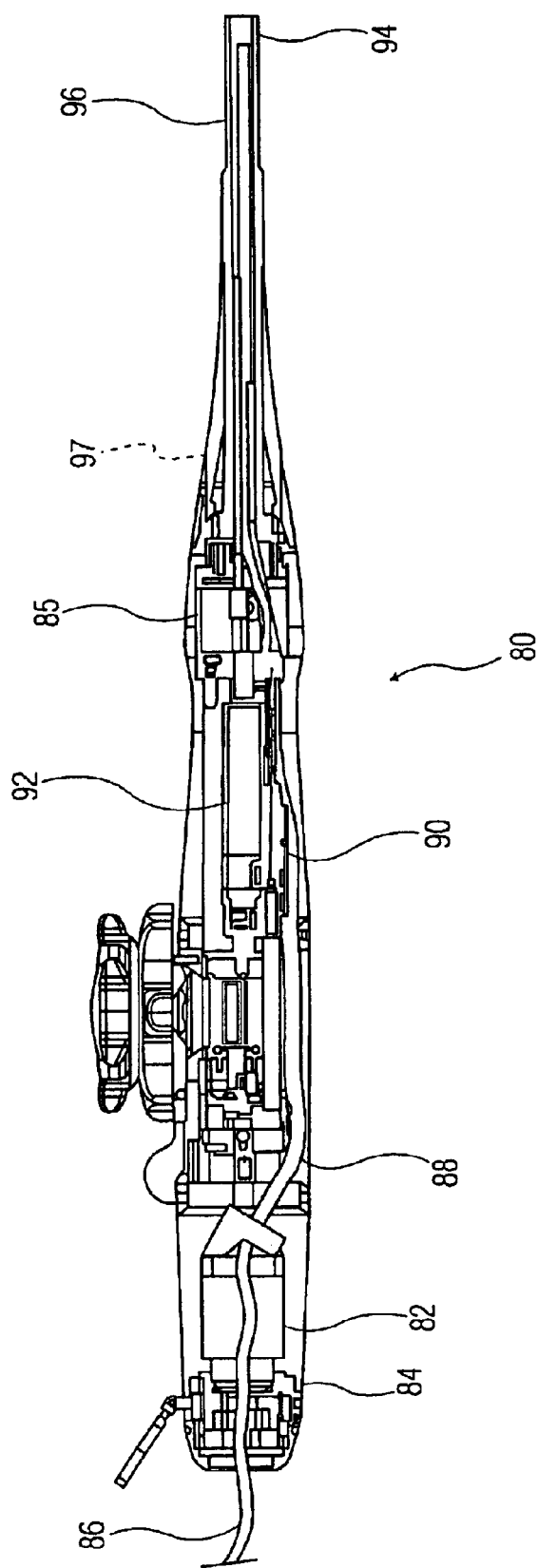
Figure 5:
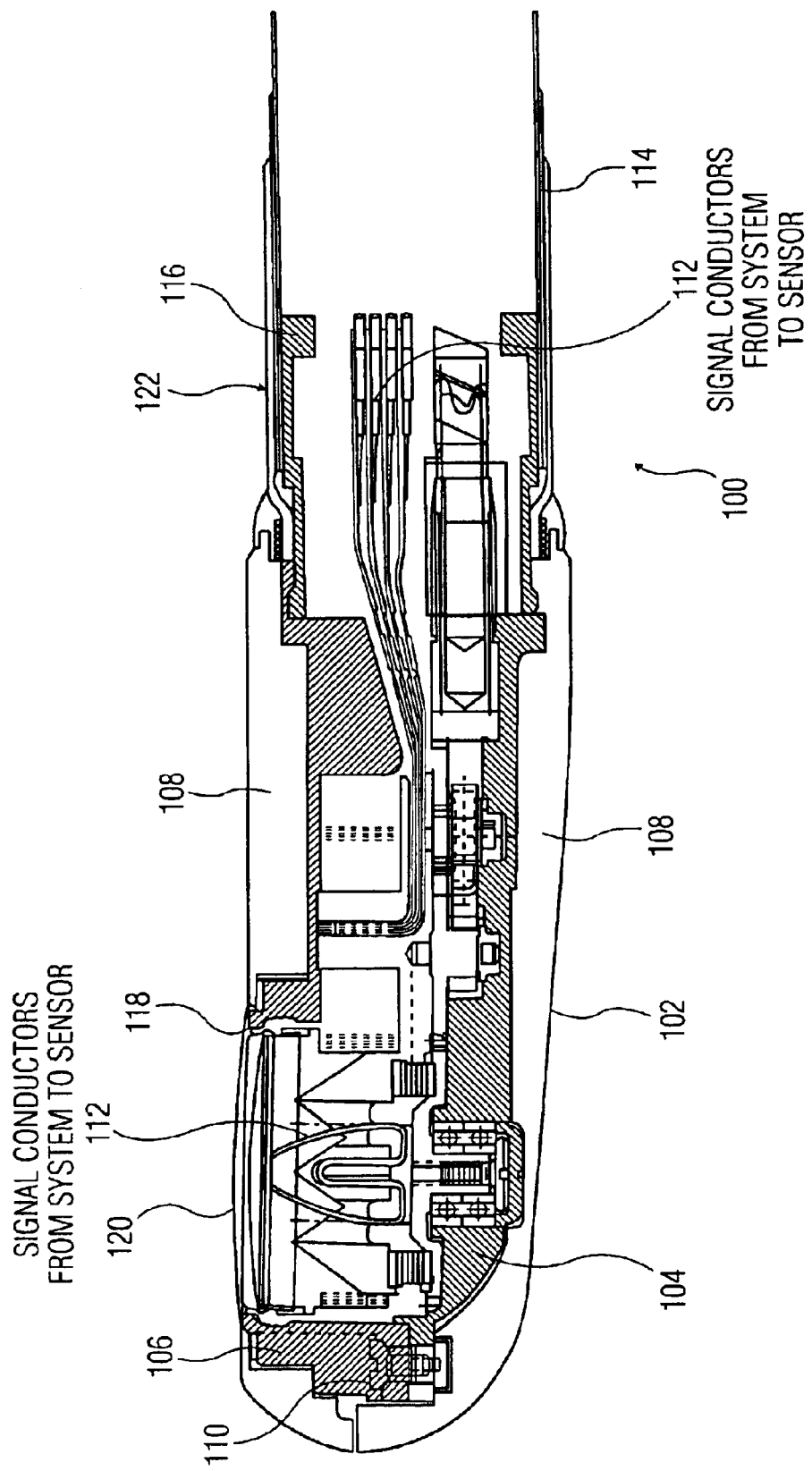

FIG. 4 is a schematic diagram of an EMI shield TEE probe of the present invention; and FIG. 5 is a schematic diagram depicting a complete EMI (or RF) shielding of a multi-plane TEE probe of this invention, wherein at least one of the transducer array, array interconnects, cabling, drive motor, drive motor connective wiring, motor drive shaft and coupling, endoscope articulation links, articulation cables, articulation compression shields and final sensor drive gearing are completely encased by shielding.

DETAILED DESCRIPTION OF THE INVENTION

The present invention teaches an ultrasound imaging system or ultrasound transducer which is entirely electromagnetically shielded. That is, all components of the transducer or system including the transducer are shielded in order that no portion is exposed to EMI, and that the shield is quite flexible in order to maintain the flexible character of, for example, an endoscope portion of an ultrasound transducer probe, such as a TEE probe.

Figure 1:
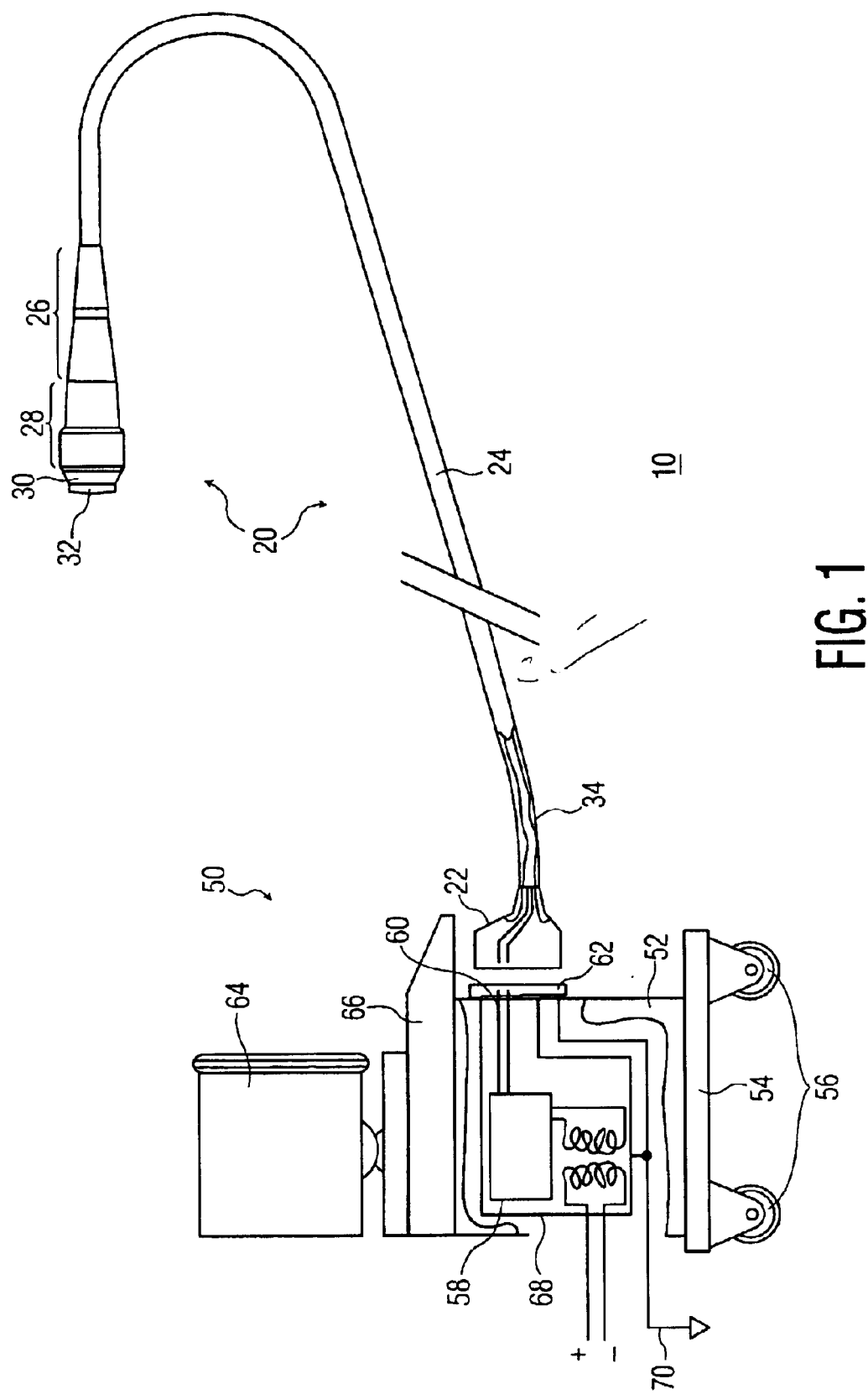

FIG. 1 shows an ultrasound imaging system 10 comprising ultrasound transducer 20 with integral EMI shielding and ultrasound console 50. The transducer includes a connector 22 at its proximal end for electrically connecting to the console. The connector 22 is attached to transducer lines or cabling 24 with lines or cabling physically connecting the connector to a transducer handle 26, and electrically connecting the connector to the transducer electronics/sensor interconnects (not shown in FIG. 1) disposed within transducer housing 28. The housing 28 mechanically connects to a sensor housing 30 (which houses the sensor components and is not shown in FIG. 1), which sensor housing mechanically connects to acoustic lens 32. An EMI or RFI shield 34 completely encloses lines/cabling. EMI shield 34 may include a portion, which extends into the transducer housing to enclose and integrally shield all of the components therein (Not shown in FIG. 1). Alternatively, the components comprising the transducer may include one or more shields in addition to shield 34, which forms contiguous protection with shield 34 (to be discussed in greater detail below).

The console 14 includes a housing 52 mounted on support 54 to which are attached wheels 56. The housing includes imaging electronics 58, internal cabling 60 and transducer connector 62. The console also includes a display 64 and keyboard 66. An electronic shield 68 surrounds all electrical systems within the housing 52, including cables 60. An EMI or RFI shield surrounds transducer connector 62, which may be part of shield 68. The electronic shield(s) in the housing may be connected to earth ground 68 (however, in a case where only floating ground is available in a system, it will suffice to connect all shields to floating ground). When connector 22 is connected to transducer connector 62, the shield 34 therein may be electrically connected to earth ground 70 via shield 58, and any other shield within the transducer electrically connected to shield 34.

Figure 2:
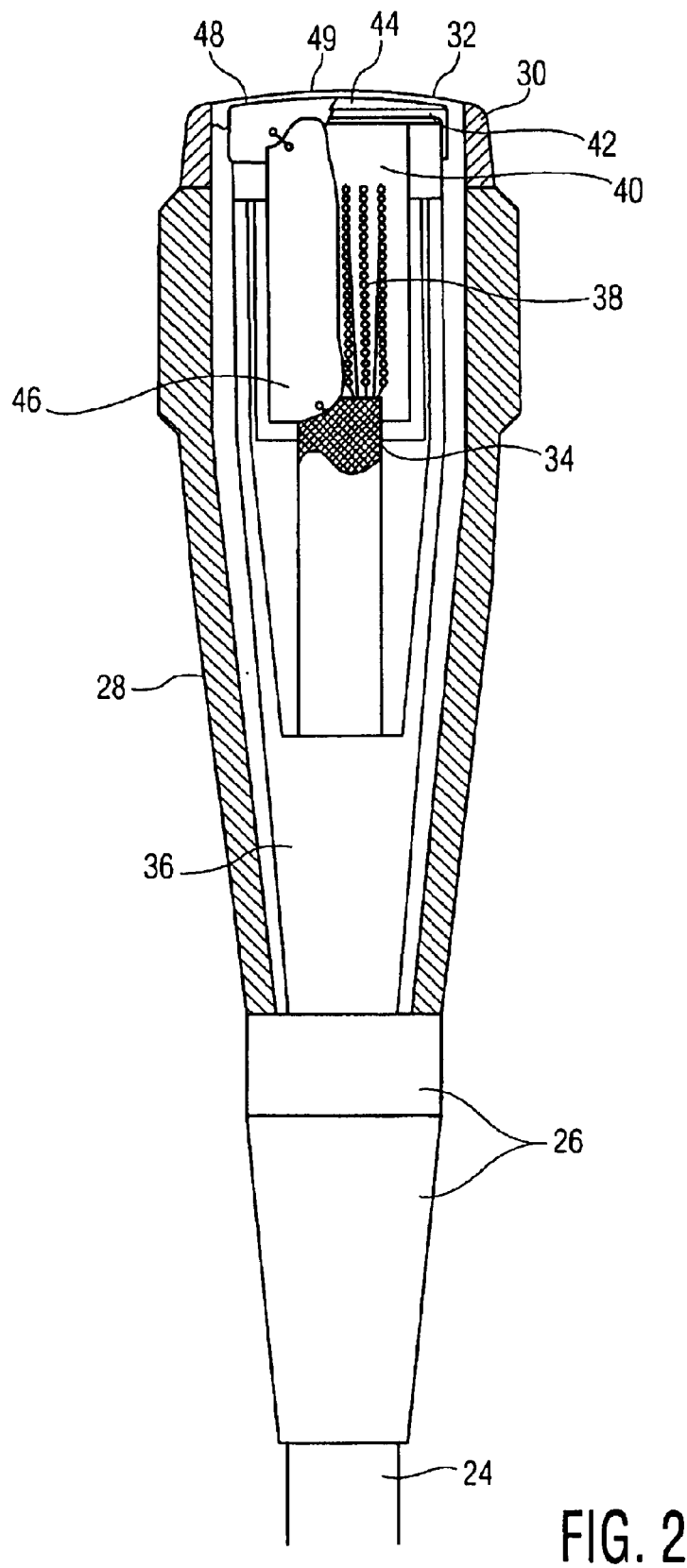

FIG. 2 shows a portion of transducer lines (or cabling) 24, the handle 26, housing, 28, sensor housing 30 and lens 32 of the transducer 20 included in the embodiment of the ultrasound imaging system 10 shown in FIG. 1. FIG. 2 also shows inner frame 36, disposed within the housing 28, and cable shield 34 extending to cable interconnects 38, which electrically connect the electrical conductors within transducer lines 24 to the sensor elements (not shown explicitly therein). Cable interconnects 38, sensor elements (which are piezoelectric elements, impedance matching layers, etc.) and other mechanical components 40 comprise the sensor. The sensor elements are mechanically connected to array stack 42. Array stack 42 is mechanically connected to inner acoustic lens 44. The sensor are enclosed with a very thin metal shield comprising foil or metalized plastic film 48, bonded to an outer surface of acoustic lens 44 (to be described in greater detail below). An EMI shield 46 is arranged to meet electrically with, or overlap thin foil or metalized film, 48, which shield 46 is electrically connected to the foil/film shield 48 and cable shield 34. Those skilled in the art should note that this is just one implementation of the protective shielding of the sensor, that is, transducer elements which is the spirit of the invention, and that any various other interconnections may also be implemented if the end result is the EM shielding. One implementation sees EMI shield 46 connected to ground when the transducer is connected via connector 62 of console 50. The outside of shielding foil/film 48 is mechanically connected to an outer acoustic lens 49.

The grounded EMI shield 46 may be any material known to those skilled in the art to exhibit the skin effect. The electrical connection to the cable shield 34, and if included, the thin foil or metalized film 48, may be implemented using conductive epoxy, solder, wire lands, etc., and may be separate components or actually extensions of the shielding and arranged in such a way that they do not exhibit antenna effects.

Figure 3A:
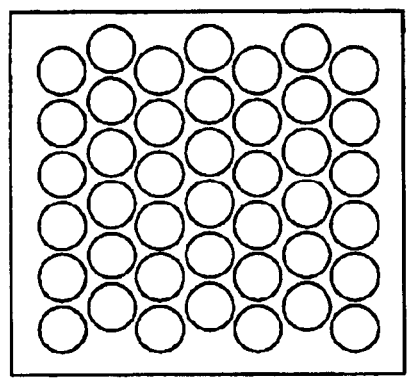
FIGS. 3C, 3D show circular and rectangular apertures which may be included in shield patterns.
FIGS. 3E, 3F show circular shield patterns comprising circular and rectangular apertures, respectively.
Figure 3B:
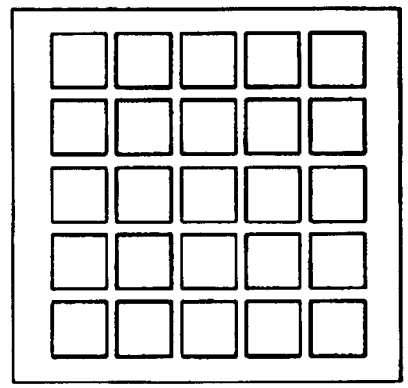
Figure 3C:
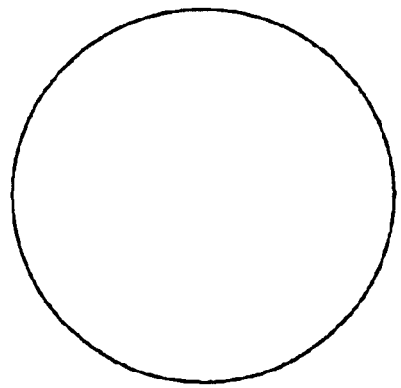
Figure 3D:
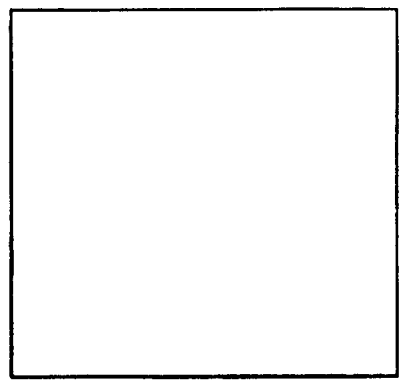
Figure 3E:
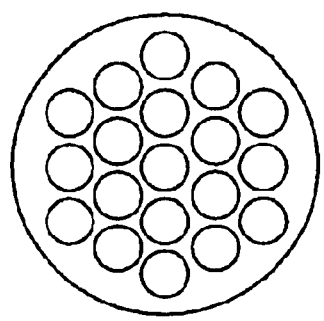
Figure 3F:
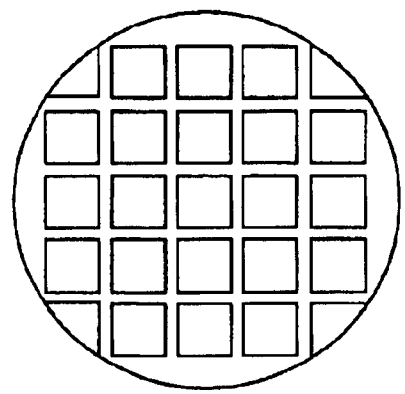

It should be noted that the thin metal foil (or metalized plastic film) and the shield 46 need not be continuous, but may be arranged with openings formed in the surface of the films in any pattern as long as any opening is no larger in any dimension than the smallest wavelength required for adequate EMI (RF) shielding anticipated herein. FIGS. 3A and 3B show examples of rectangular sensor metal foils or plastic films which may be used as shield 48, in the circular and rectangular shielding patterns highlighted in FIGS. 3C and 3D, respectively. FIGS. 3E and 3F show circular foils/films which may be used with rectangular and circular shield patterns of FIGS. 3D and 3C, respectively. The preferred design of both the shield and foil/film should exhibit acoustic transparency and be constructed to a thickness of about 100 microns or less. One embodiment is 100 microns. The EMI shield 46 may be flexible or rigid as a function of transducer design requirements. The EMI shield, however, must cover continuously all signal and control circuits within the transducer. As mentioned above, while a rigid shield 46 is preferable, metal foils such as those comprising foil/film 48 may be used around the transducer or sensor array rather than a machined or pre-formed metal housing.

U.S. Pat. No. 6,364,828, commonly owned and incorporated by reference herein, teaches an articulated elongated inspection neck to shield RF interference. The patent describes a flexible bending neck region of a TEE endoscope which incorporates full shielding around ultrasound signal lines in a controlled articulatable assembly Connected by solder or conductive epoxy proximal the bending neck is the flexible insertion tube. The insertion tube construction is metal braid over metal monocoil (shield). Placed over the neck is a de-expanded PVC layer, which is overlayed by a polyolefin heat shrink tube, which is overlayed by urethane. The plastic layers provide electrical isolation while the metal provides shielding, in unison for flexibility.

FIG. 4 shows an embodiment of a TEE transducer probe handle 80 constructed in accordance with the spirit of this invention. The TEE probe 80 includes a complete EMI (or RF) shield, where the probes' sensor array, array interconnects, cabling, drive motor, drive motor connective wiring, motor drive shaft and coupling, endoscope articulation links, articulation cables, articulation compression shields and final sensor drive gearing are completely encased by shielding, whether a singularly constructed Faraday cage, or as a composite of shield portions, with or without overlap, and electrically connected to each other is such a manner that the impedance to current which might flow between portions is a minimum to maximize EMI protection over the entire system. Preferably, all components comprising the TEE probe are completely shielded.

A proximal RFI box 82 is included in a probe housing 84, which box contains an ultrasound cable motor power and encoder interface (not shown explicitly). A distal RFI box 85 is shown which contains a drive coupling drive shaft, articulation cables and sheaths shielded. A ultrasound coaxial cable 86 is shielded in a metal braid connected to the proximal RFI box. A shielded ultrasound coaxial cable bundle 88 is clamped to the distal RFI boxes. A shielded multiplane drive motor/encoder interface PCB, with external switch interface 90 is shown. A multiplane drive motor 92 is shown shielded inside a continuous housing. A continuous braid from the distal articulation linkage is shown, which braid is bonded with conductive epoxy of solder to distal RFI box. Outer insertion tube insulation layers 96 are shown. FIG. 4 also clearly shows a boundary 97 where the probe housing ends at an endoscopic portion of the probe, i.e., that portion to the right of boundary 97. While the shielding provided around all cabling and conductors within the probe must be flexible, it is paramount that the shielding within the gastroscopic portion of any transducer probe, e.g., TEE probe, be flexible to maintain the flexible character of the same gastroscopic portion.

All aforementioned components are shielded. That is, all the aforementioned components are surrounded by a Faraday cage or continuous shield to significantly reduce any potential antenna effect of the components seeing currents generated by electromagnetic fields in general, and electrosurgical units, such as cauterizing units, in particular.

FIG. 5 shows a preferred embodiment of a TEE probe 100 of this invention, including a shielding construction wherein all the mechanical and electrical components comprising the TEE probe are surrounded by an enclosed metal cage (shown cutaway in the figure). Preferably, the metal cage entirely enclosing the probe is closed continuously. However, as mentioned above, continuous shielding is not necessary for effective shield as long as the largest dimension of any aperture is smaller than the smallest wavelength (highest frequency) of the noise source anticipated to be in use proximate the probe, e.g. a cauterizing ESU. Those skilled in the art realize that the spirit of the invention resides in the fact that entirely protectively shield the TEE probe from EMI (or RFI) reduces any antenna effects of components seeing currents, particularly form ESU fields, and transferring same currents to ultrasound lines, components, etc., by electrical connection or electromagnetic coupling.

More particularly, FIG. 5 shows TEE probe 100 including a metal housing frame 102 enclosing a metal lower housing 104, a metal upper housing 106, plastic caps bonded over metal housings for outer insulation and housings 110 screwed together for continuous electrical shielding. Signal conductors 112 are included to electrically connect sensors to an ultrasound system (not shown). A metal braid or double counter wound monocoil 114 is shown soldered to end fittings on the metal housing frame. Split housings 116 are shown clamped over a terminator with a braid or double monocoil soldered for continuous shielding. A metalized plastic film 118 is shown stretched over and conductively epoxied to a metal housing. An outer flexible insulation layer 122 is shown proximate housing 102.

The FIG. 5 embodiment may further include that the drive motor power/switch interface may employ a motor control comprising a printed circuit board with active ESU isolation circuitry. Such a design must incorporate a controlled shield, e.g., ESU shielding, and isolation circuitry, e.g., ESU isolation circuitry, on a common PCB. Those skilled in the art will see that the FIG. 5 TEE probe 100 may be multiline or matrix in design, that is a matrix TEE probe such as set forth in U.S. Pat. No. 6,126,602, commonly owned and incorporated herein by reference. Other designs may include matrix array TEE probes, or any other transducer probe design known to those skilled in the art as long as all components are completely shielded, for example, but not limited to a front face of the matrix array, the array interconnects, control electronics, etc., and electrical communication means included therein.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. An electromagnetically protected ultrasound transducer, comprising:
    a transducer housing including an imaging sensor, an outer acoustic lens, a cable interconnect and an internal metal shield which surrounds the sensor and cable interconnect; and
    a cable including electrical conductors and electromagnetic cable shielding, the electrical conductors electrically connected to the cable interconnect at a first end, and the electrical conductors and the cable shielding are electrically connected to a transducer connector at a second end, wherein the cable shielding is electrically connected to earth ground via at least a shield surrounding the transducer connector;
    wherein further included in the transducer housing is a thin electromagnetic shield, internal to the outer acoustic lens, and electrically connected to one of the internal metal shield and cable shielding such that all elements inside a boundary formed by the transducer housing and outer acoustic lens are substantially electromagnetically protected from external electromagnetic radiation, and that the electromagnetically protected transducer maintains its flexibility for its intended purpose.

2. The ultrasound transducer set forth in claim 1, wherein the thin electromagnetic shield comprises a thin metal foil.

3. The ultrasound transducer as set forth on claim 1, the internal metal shield is flexible.

4. The ultrasound transducer set forth in claim 2, wherein the thin metal foil is less than 100 microns.

5. The ultrasound transducer set forth in claim 2, wherein the thin metal foil is less than 1 mm. in thickness.

6. The ultrasound transducer set forth in claim 1, wherein the thin electromagnetic shield comprises a thin metalized plastic film.

7. The ultrasound transducer set forth in claim 2, wherein the thin electromagnetic shield includes openings, which are less than a wavelength of the highest frequency electromagnetic radiation from which the transducer is intended to be protected.

8. The ultrasound transducer set forth in claim 1, wherein the intended electromagnetic radiation from which the transducer is intended to be protected includes that radiation generated by an electro-surgical unit.

9. The ultrasound transducer set forth in claim 8, wherein the thin electro-surgical unit is a cauterizing unit.

10. The ultrasound transducer set forth in claim 7, wherein the thin electromagnetic shield is constructed to have a length and width of any practical dimension, including, but not limited to circular and rectangular.

11. The ultrasound transducer set forth in claim 1, wherein the internal metal shield may be one of rigid and flexible in accordance with the transducer design requirements.

12. The ultrasound transducer set forth in claim 1, wherein the thin electromagnetic shield is electrically connected to the internal metal shield by one of conductive epoxy and solder.

13. The ultrasound transducer set forth in claim 1, wherein the housing comprises the internal metal shield.

14. The ultrasound transducer set forth in claim 1, wherein a portion of the thin metal shield is mechanically connected to an inner portion of the outer acoustic lens.

15. An electromagnetically protected ultrasound Transesophageal echocardiograph (TEE) probe, comprising:
    a probe housing including an imaging sensor, an outer acoustic lens, a cable interconnect and an internal metal shield which surrounds the sensor and cable interconnect; and
    a cable including electrical conductors and electromagnetic cable shielding, the electrical conductors electrically connected to the cable interconnect at a first end, and the electrical conductors and the cable shielding are electrically connected to a transducer connector at a second end, wherein the cable shielding is electrically connected to earth ground via at least a shield surrounding the transducer connector;
    wherein the internal metal shield is electrically connected to the cable shielding such that all elements inside a boundary formed by the transducer housing and outer acoustic lens are substantially electromagnetically, protected and flexibility of the TEE probe, including any endoscopic portion, is maintained as required for effective operation.

16. The TEE probe set forth in claim 15, wherein the internal metal shield includes openings, which are less than a wavelength of the highest frequency electromagnetic radiation from which the transducer is intended to be protected.

17. The TEE probe set forth in claim 16, wherein the intended electromagnetic radiation from which the transducer is intended to be protected includes that radiation generated by an electro-surgical unit.

18. The TEE probe set forth in claim 16, wherein the thin electro-surgical unit is a cauterizing unit.

19. The TEE probe set forth in claim 15, wherein the housing includes a drive motor, drive motor connection wiring, motor drive shaft and coupling, endoscope articulation links, articulation cables, articulation compression sheathing and final sensor drive gearing.

20. The TEE probe set forth in claim 19, wherein the metal shield comprises a metal cage surrounding all elements housed within the housing but for the outer acoustic lens.

21. The TEE probe set forth in claim 20, further including one of a thin metal foil and metalized plastic film included in the housing to surround all the internal components therein but for the outer acoustic lens, and electrically attached to one of the internal metal shield and cable shielding in order to supplement the electromagnetic protection provided by the internal metal shield.

22. The TEE probe set forth in claim 19 further includes a drive motor power/switch interface including a motor control PCB with active electromagnetic shielding electrically connected to one of the internal metal shield and cable shielding.

23. The TEE probe set forth in claim 15, wherein the internal metal shield may be on of rigid and flexible in accordance with the transducer design requirements.

24. The TEE probe set forth in claim 21, wherein the housing comprises the internal metal shield.

25. The TEE probe set forth in claim 15 constructed to operate as one of a multiplane and matrix TEE probe.

26. An ultrasound imaging system comprising an electromagnetically protected ultrasound transducer, a display for displaying ultrasound images, a housing including a transducer connector including at least one connection for connecting to earth ground and a computer for processing electrical signals representative of received ultrasound echoes, wherein the ultrasound transducer comprises:

a transducer housing including an imaging sensor, an outer acoustic lens, a cable interconnect and an internal metal shield which surrounds the sensor and cable interconnect; and a cable including electrical conductors and electromagnetic cable shielding, the electrical conductors electrically connected to the cable interconnect at a first end, and the electrical conductors and the cable shielding are electrically connected to a transducer connector at a second end, wherein the cable shielding is electrically connected to earth around via at least a shield surrounding the transducer connector;

wherein further included in the transducer housing is a thin electromagnetic shield, internal to the outer acoustic lens, and electrically connected to one of the internal metal shield and cable shielding such that all elements inside a boundary formed by the transducer housing and outer acoustic lens are substantially electromagnetically protected from external electromagnetic radiation, protected and flexibility of the transducer is maintained as required for effective operation.

27. An ultrasound imaging system comprising an electromagnetically protected ultrasound TEE probe, a display for displaying ultrasound images, a housing including a transducer connector including at least one connection for connecting to earth ground and a computer for processing electrical signals representative of received ultrasound echoes, wherein the ultrasound TEE probe comprises:

a probe housing including an imaging sensor, an outer acoustic lens, a cable interconnect and an internal metal shield which surrounds the sensor and cable interconnect; and a cable including electrical conductors and electromagnetic cable shielding, the electrical conductors electrically connected to the cable interconnect at a first end, and the electrical conductors and the cable shielding are electrically connected to a transducer connector at a second end, wherein the cable shielding is electrically connected to earth around via at least a shield surrounding the transducer connector;

wherein the internal metal shield is electrically connected to the cable shielding such that all elements inside a boundary formed by the transducer housing and outer acoustic lens are substantially electromagnetically protected, protected and flexibility of the TEE probe, including any endoscopic portion, is maintained as required for effective operation.

28. The ultrasound imaging system set forth in claim 27, wherein the TEE probe is constructed to operate as one of a multiplane, matrix and matrix array TEE probe.

* * * * *